United States Patent
Bayon et al.

(10) Patent No.: US 12,318,533 B2
(45) Date of Patent: *Jun. 3, 2025

(54) SURGICAL DRAIN

(71) Applicants: Sofradim Production, Trevoux (FR); CEA (Commissariat A L'energie Atomique Et Aux Ener, Paris (FR)

(72) Inventors: Yves Bayon, Lyons (FR); Dagmar Guyader, Chaleins (FR); Maxime Gougis, Grenoble (FR); Severine Vignoud, Bernin (FR); Frederic Bottausci, Saint Egreve (FR); Pascal Mailley, Villages du Lac de Paladru (FR)

(73) Assignees: SOFRADIM PRODUCTION, Trevoux (FR); CEA (Commissariat A L'energie Atomique Et Aux Energies Alternatives, Paris (FR)

( * ) Notice: Subject to any disclaimer, the term of this patent is extended or adjusted under 35 U.S.C. 154(b) by 1142 days.

This patent is subject to a terminal disclaimer.

(21) Appl. No.: 17/180,347

(22) Filed: Feb. 19, 2021

(65) Prior Publication Data
US 2021/0178131 A1  Jun. 17, 2021

Related U.S. Application Data (63) Continuation of application No. 15/968,028, filed on May 1, 2018, now Pat. No. 10,953,207.

(30) Foreign Application Priority Data

May 23, 2017 (EP) .................................. 17305602

(51) Int. Cl.
*A61M 1/00* (2006.01)
*A61M 27/00* (2006.01)

(52) U.S. Cl.
CPC ................ *A61M 1/84* (2021.05); *A61M 1/90* (2021.05); *A61M 27/00* (2013.01);
(Continued)

(58) Field of Classification Search
CPC ...... A61M 39/0208; A61M 1/74; A61M 1/96; A61M 1/982; A61M 1/84; A61M 27/00;
(Continued)

(56) References Cited

U.S. PATENT DOCUMENTS 4,681,559 A * 7/1987 Hooven ............. A61M 27/006
604/9
10,953,207 B2 3/2021 Bayon et al.
(Continued)

FOREIGN PATENT DOCUMENTS

WO 2009071926 A1 6/2009

OTHER PUBLICATIONS

Extended European Search Report issued in corresponding EP17305602.9 dated Nov. 28, 2017, 7 pages.

*Primary Examiner* — Ariana Zimbouski
(74) *Attorney, Agent, or Firm* — Weber Rosselli & Cannon LLP (57) ABSTRACT

In a surgical drain system formed with two or more branches, exudate flow from a patient's wound is directed between two branches with the respective filling and emptying times determined in order to identify the presence of a blockage in the drain.

20 Claims, 6 Drawing Sheets

(52) U.S. Cl.
CPC .  *A61M 2205/18* (2013.01); *A61M 2205/3303* (2013.01); *A61M 2205/3331* (2013.01); *A61M 2205/3334* (2013.01); *A61M 2205/3389* (2013.01); *A61M 2205/52* (2013.01); *A61M 2205/581* (2013.01); *A61M 2205/583* (2013.01)

(58) Field of Classification Search
CPC .......... A61M 27/06; A61M 2205/3334; A61M 2205/3389; A61M 2205/18; A61M 2205/3303; A61M 2205/52; A61M 2205/581; A61M 2205/583; A61F 13/05
See application file for complete search history.

(56) References Cited

U.S. PATENT DOCUMENTS

| | | | |
|---|---|---|---|
| 2006/0173253 A1 | 8/2006 | Ganapathy | |
| 2013/0150813 A1 | 6/2013 | Gordon | |
| 2014/0058344 A1 | 2/2014 | Toth | |
| 2015/0094644 A1* | 4/2015 | Lenihan | A61M 39/24 604/9 |
| 2016/0296690 A1* | 10/2016 | Kume | A61M 39/06 |
| 2017/0165406 A1 | 6/2017 | Chien | |

\* cited by examiner

SURGICAL DRAIN

CROSS-REFERENCE TO RELATED APPLICATIONS

This application is a Continuation Application of U.S. patent application Ser. No. 15/968,028, filed on May 1, 2018, which claims the benefit of and priority to European Patent Application Ser. No. 17305602.9, filed on May 23, 2017, the entire disclosures of which are incorporated by reference herein.

BACKGROUND

This invention relates to a surgical drain for use in medical applications and a method.

SUMMARY

A number of surgical procedures require a patient to be provided with a surgical/medical drain to aid recovery. Surgical drains are medical devices used to provide a connection to a body cavity to allow fluids to flow out of the patient to a collection vessel. The drained fluids can include pus, blood or other fluids which gather at a wound site and could become a focus for infection or retained blood complications. The drained fluid is sometimes referred to as "exudate". The drain remains in place until the exudate flow has stopped, or has become less than a predetermined volume, for example, 25 ml per day. In order to assist the healing process, it is also known to gradually withdraw the drain from the wound by 2 cm per day, thus facilitating healing whilst maintaining the draining of the wound.

The fluid may be drawn from the wound by gravity or assisted by use of an active surgical drain utilising a vacuum pump.

Surgical drains may be made from a variety of materials to cater for a range of procedures. Typically, these are PVC, rubber or silicone formed into a tube of a diameter of 2 to 6 mm and may range in length from 50 to 100 cm.

The form of the exudate provides a useful indication of the healing process. The exudate is monitored as to its colour and consistency since that may indicate a change in the patient's condition. For example, a sudden change in the colour of the exudate to be more "bloody" and more profuse may indicate a haemorrhage. A change from thin and pink to thick and brown could indicate faecal material leaking into the wound and a colour change to green may indicate infection and the potential for sepsis.

Monitoring the exudate is therefore very important but it will also be appreciated that monitoring by nursing staff is time consuming and, between inspections, it is possible for conditions to arise which are not discovered for many hours until the next scheduled inspection takes place. This delay may have serious consequences for the patient, as remedial treatment to correct a post-operative condition, such as an infection, is delayed.

Another issue experienced, is that the exudate flow may drop for reasons not associated with there being less material in the wound to be drained. For example, the drain may become clogged, and the flow reduced, even though the wound itself still needs draining. This can lead to the drain being removed too early from the patient in the false belief that the wound is healing.

It has been proposed to provide drains with sensors to monitor the exudate flow. However, such sensors are sometimes inaccurate as a result becoming "fouled" by materials in the exudate or by blockage of the drain.

The present invention arose in an attempt by the inventors' to alleviate the problems associated with blockage or obstruction of a surgical drain.

According to the invention there is provided, a surgical/medical drain comprising at least a first branch and a second branch; a flow controller operative to in use control flow through the branches and means to monitor the rate of flow therethrough; a comparator to compare the respective rates of flow through the first and the second branch and to provide an output representative thereof.

By providing at least a first and second branch and controlling the flow therethrough, the flows may be compared to determine the presence of a blockage downstream of the branches. In particular, if a first branch is filling at a rate faster than the other branch is emptying then the downstream section is blocked. The rate of difference between filling and emptying of the branches will depend on the severity of the blockage. More than one branch is required but more than two branches, three or more, may also be utilised to provide some element of redundancy, for example, to cater for one branch or its associated sensors and flow control failing. Two branches are provided in the described embodiment.

Preferably, an alarm device is provided which is responsive to the output to provide an alarm. The alarm may be an audible alarm, a visual alarm or combination of the two which may be presented to a user of the system or provided to another system.

Preferably, respective input and output valves are provided to control the flow through the branch under the control of the flow controller.

In the described embodiment, which is preferred, the valves control input and output from the branches. But other means are envisioned. For example, the valve action may be provided by a magneto-strictive element operable to reduce the diameter of the branch. Such an element may be provided about a wall defining the branch to constrict the branch or integrally formed within the branch. In the described embodiment, an inlet valve is opened and an outlet valve is closed to allow the branch to fill. The other branch is opened at the same time to allow it to empty. This is done by closing the inlet valve to prevent exudate flowing into that branch and the outlet valve is opened to allow the branch to empty into the next section of the drain. In the described embodiment, which is preferred, the valves open and close in a binary fully open fully closed manner but in alternative embodiments the valves may open proportionally, that is to say, partly opened and partly closed.

There will be many ways in which the state of fill of the branches may be sensed. The sensors may be resistive sensors, capacitive sensors, reactive sensors, or optical or other sensors or combinations of these. The sensors may be formed on arrays attached to an outer or inner surface of the branches. The sensors may also be integrally formed with the branch by fabrication and deposition techniques. Preferably, the sensors comprise level sensors within the branches to provide an output indicative of the level of exudate within the branch. For certain sensors such as optical sensors the branch may be made transparent to allow the sensing of the level from a position exterior of the branch.

In order to determine the exudate flow conditions, preferably, the drain further comprises logic means to determine an alarm condition when one of the branches fills more quickly than the other empties. This may be formed from discrete logic devices or application specific integrated circuits, ASICs, or by provision of a suitably programmed microprocessor configured to follow a software program provided as a set of machine code language instructions held in memory.

The program may be provided in preloaded read only memory (ROM) or downloadable from a network or storage device such as a USB or disc. In the described embodiment, a number of processing functions are described as separate blocks but it will be appreciated by the person skilled in the art that these may be provided on one or more processors. That is to say, one processor may be programmed to provide more than one of the blocks of functionality.

In the described embodiment, the branches are described as "tanks". They are broader than the remaining sections of the drain in order to accommodate a plurality of level sensors and to provide a larger volume to accept the exudate flow but need not be so. That is to say, the tanks may have the nominally same diameter as the adjacent part of the drain. The tanks may be provided joined or formed together or as separate components.

Preferably, the branches or tanks are of a known ratio of volumes but, most preferably, the tanks are nominally identical volume. This is preferred as it will simplify the processing in determine the respective rates of filling and emptying.

One end of the drain will be configured to facilitate insertion into a patient and the other end may be configured for connection to a receptacle for the drained fluids. A vacuum may be applied to the receptacle to encourage the exudate flow along the drain.

Advantageously, additional sensors may be provided to monitor the flow from the patient and at intermediate positions before the branches of the drain. This will enable the flow to be monitored at those positions to determine blockages prior to the branches or tanks. In the described embodiment the additional sensors are provided at that part of the drain to be inserted into the patient and at a position intermediate that part and the branches. This will allow the inflow from the patient to be monitored and to be compared to the flow present at the intermediate part. This may be used to determine a blockage being present before the branches.

The invention provides in a further aspect a method of determining the presence of a blockage in a surgical drain in accordance with the first aspect of the invention comprising the steps of, directing an exudate flow away from a first branch to a second branch in the drain to fill the second branch, directing an exudate flow from the first branch to an output from the drain to empty that branch, comparing the rate of filling of the second branch with the rate of emptying of the first branch to determine a blockage condition.

Preferably, the method further comprises the step of providing an alarm when a blockage is determined. The step of directing flow includes opening inlet and outlet valves controlling the flow within respective branches. Then the rate of filling and emptying is determined by reading level sensors determining the level of exudate in respective branches for a given time interval.

A data carrier such as a computer disc, memory stick or memory card may store a set of computer implementable instructions for carrying out the method. This may be used to program the system to perform the method by connection via a suitable port such as a USB port or from a drive or over a network.

BRIEF DESCRIPTION OF THE DRAWINGS

Specific embodiments of the invention will now be described with reference to the drawings of which.

DETAILED DESCRIPTION

Figure 1:
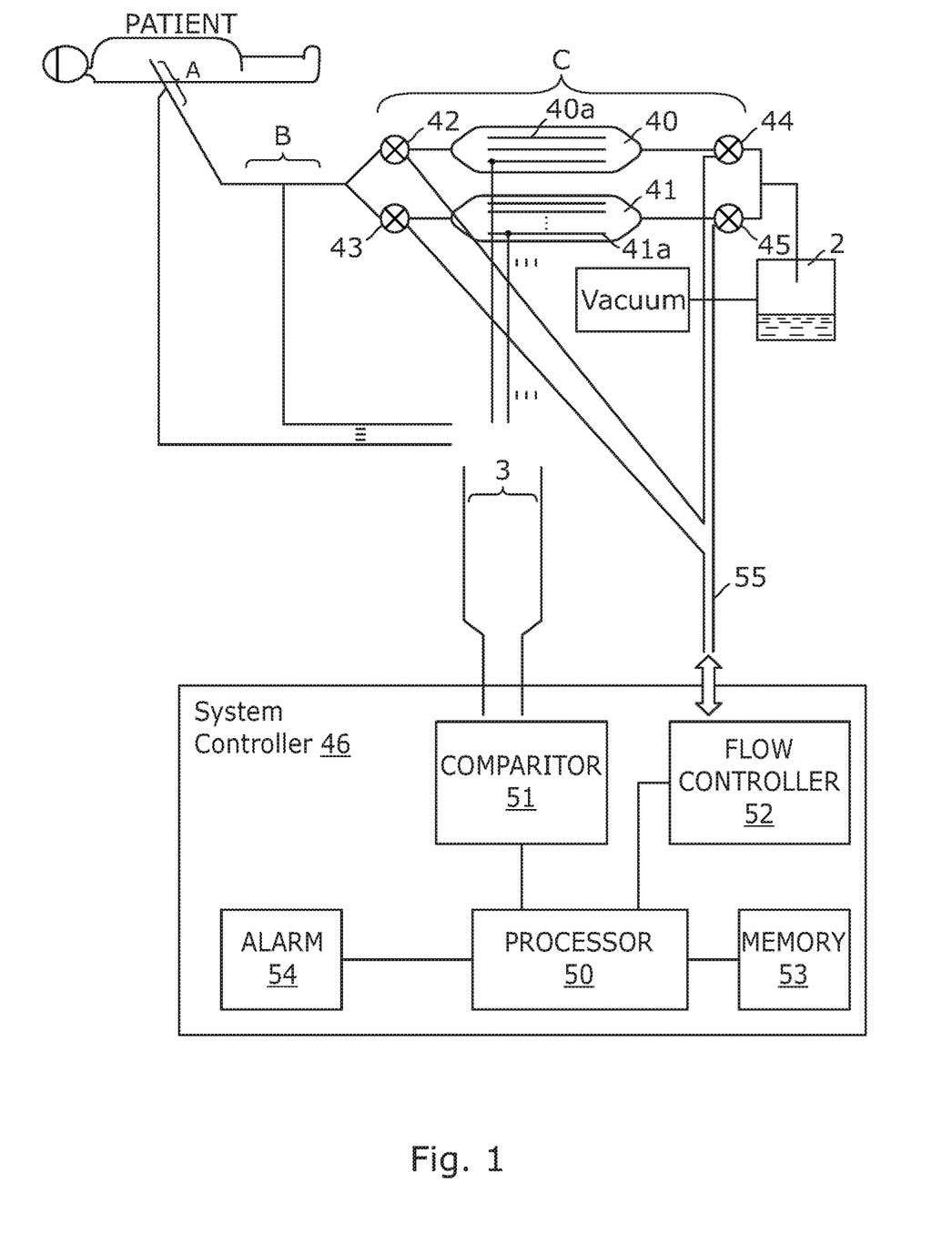
FIG. 1 shows a drain system in accordance with an embodiment of the invention inserted into a patient having a wound requiring draining.

As is shown schematically in FIG. 1, a drain system 1 in accordance with an embodiment of the invention comprises three distinct parts, A, B and C. Part A is that part of the drain which interfaces with the patient body by insertion into the body. This part may be several millimetres to a few centimetres long. Part B is the length of drain tube intermediate the patient's body and a flow meter provided as part C. The drain tube 2 is of a familiar type being formed from a medical grade silicone material having a diameter of 5 mm. Exudate is conducted from the patient by the drain to pass through part A, B and then through part C to be deposited into a collection vessel or bag 2.

Figure 2:
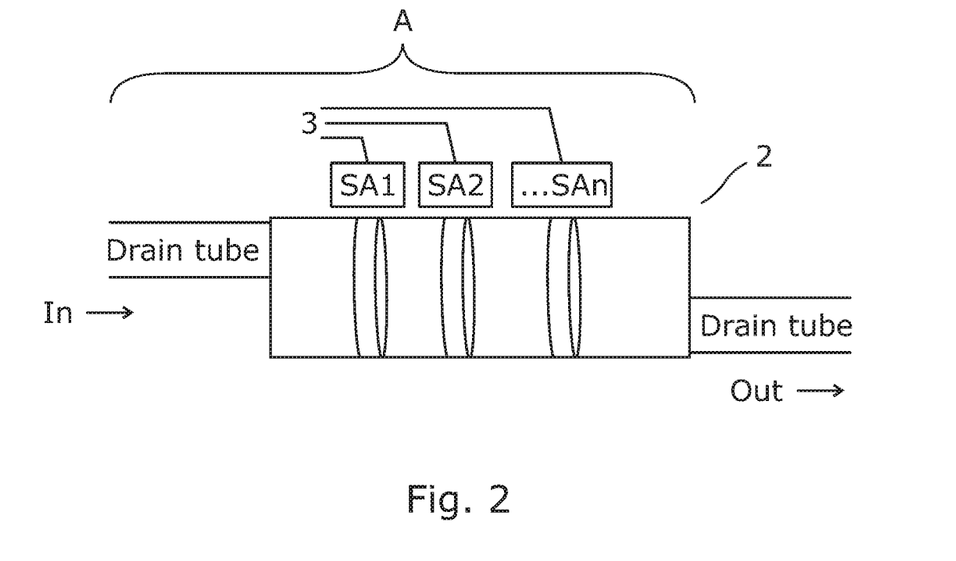
FIG. 2 shows in greater detail a first part of the drain system shown in FIG. 1 with further detail of a sensor arrangement.

Part A is shown in greater detail in FIG. 2. It includes a number of sensors SA1 to SAn located within a section of the drain tube 2. In the figure, the drain tube containing the sensors is shown having a greater diameter than the inlet and outlet part of the tube but it will be appreciated that the diameter of the drain tube may, in alternative embodiments, be substantially the same. The sensors are connected to a sensor bus 3 and from there to a processor.

Figure 3:
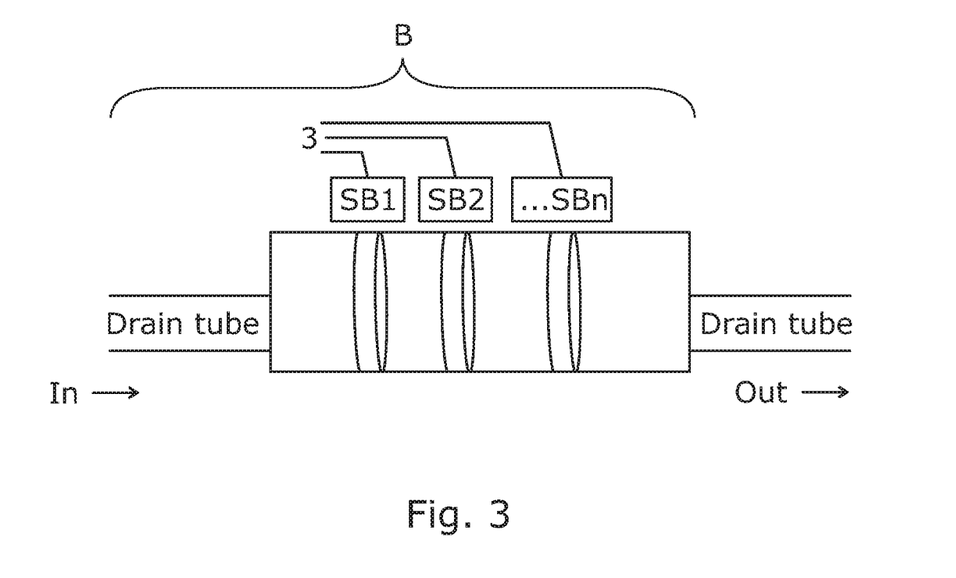
FIG. 3 shows in greater detail an intermediate part of the drain system shown in FIG. 1 with further detail of a sensor arrangement.

Part B also includes a similar arrangement of sensors SB1 to SBn again connected to a sensor bus 3 and to the processor.

The outputs from the sensors from parts A and B can be used to determine if there is a blockage along these sections of the drain by comparison of the respective flow rates as will be appreciated by a person skilled in the art without further elaboration.

Figure 4A:
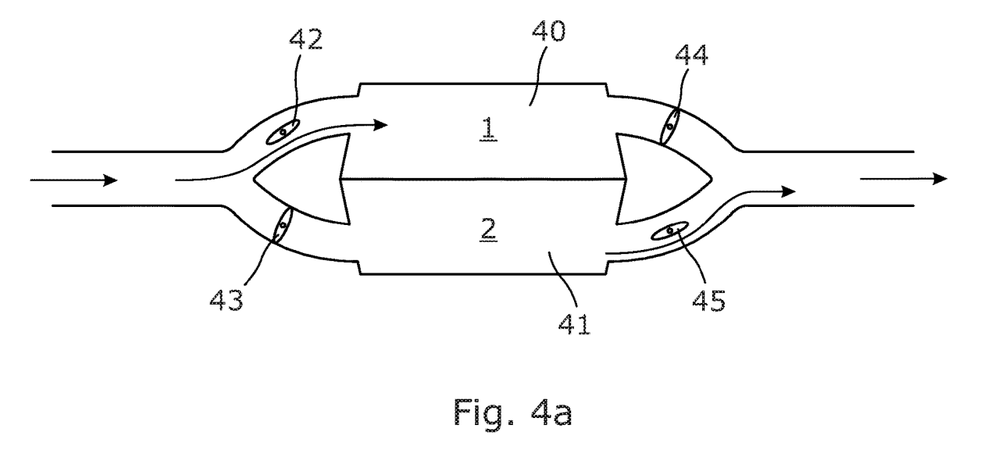
FIGS. 4a, 4b and 5 show branches formed by tanks of the drain system as seen in FIG. 1 with respective flow control valves for controlling the flow of exudate into and out of the tanks.

Part C is formed of two or more tanks arranged in parallel and a valve arrangement for controlling the filling of the tanks as is shown in FIG. 4. They form branches in the drain though which the exudate may flow. The tanks 40, 41 are formed of plastics material to have matching volumes. In this particular embodiment, the tanks have a volume of 2 ml although other volumes may be used or ratios of volumes. This particular volume is useful as it allows a measurement to be taken of the exudate level every 15 minutes for a flow rate of 100 ml per 24 hour period with each measurement being of approximately 1 ml per 15 minute period.

Located at the entrance and exit of each tank is an inlet valve 42, 43 and an outlet valve 44, 45. The valves 42 to 45 are motorised valves operated by a control system 46. The control system 46 is microprocessor based operating in accordance with machine executable code stored in local memory. Its structure and method of operation will be later described.

Each of the tanks 40, 41 is provided with a plurality of sensors 40a and 41a mounted to the internal wall as shown in FIG. 1. Each sensor can provide an output of the level of exudate within the tank as the exudate builds up (level increases). The sensors are connected to the control system 46 over the sensor bus 3.

The flow control system 46 monitors each of the sensors and determines if there is an abrupt change in flow conditions. If such is detected, a downstream flow obstruction check process is performed. In this, the valves 42 to 45 are selectively opened and closed in a synchronised manner under the control of the flow control system 46 to determine the presence of an obstruction. This will be more fully described later after an overview of the system is given.

Reverting now to FIG. 1, the control system 46 includes a processor 50, a comparator 51, a flow controller 52, a memory 53 and an alarm 54. The memory 53 is provided as a combination of Read Only Memory (ROM) and Random Access Memory (RAM) to hold data and a program as a set of executable code instructions to govern the system operation under the processor 50.

The comparator 51 is connected to the sensor bus 3. It reads each of the sensors and performs a comparison to determine the respective flow rates throughout the parts A, B and C, and to deduce therefrom if there are any blockages. In the event that a blockage is determined then an output is provided to the processor 50 which instructs the alarm 54 to give an audible and visual alarm signal to warn nursing staff.

The flow controller 52 is connected to a valve control bus 55 to provide control output to each of the valves 42 to 45. The bus also allows status information for the valves to be passed back to the flow controller. The flow controller 52 operates as instructed by the processor 50 to control the selection of the tanks to fill or empty in accordance with the predetermined scheme as referred to earlier by opening and closing valves in a synchronised manner. That is to say, valves 42 and 44 are operated at the same time such that when valve 42 is opened valve 44 is instructed to close and when valve 42 is instructed to close, valve 44 is instructed to open. Similarly, when valve 43 is instructed to open, valve 45 is instructed to close and when valve 43 is instructed to close, valve 45 is instructed to open. To fill a tank, the inlet valve is opened and the outlet valve is closed, that is to say, valves 42, 43 are opened and valves 44 and 45 are closed when their respective tanks are to be filled. To empty a tank, the valves 42, 43 are closed and valves 44, 45 are opened.

In normal operation the tanks are opened and allowed to fill or closed and allowed to empty in an alternating manner. That is to say, when tank 40 is to be filled tank 41 is to be emptied and vice versa.

Figure 4B:
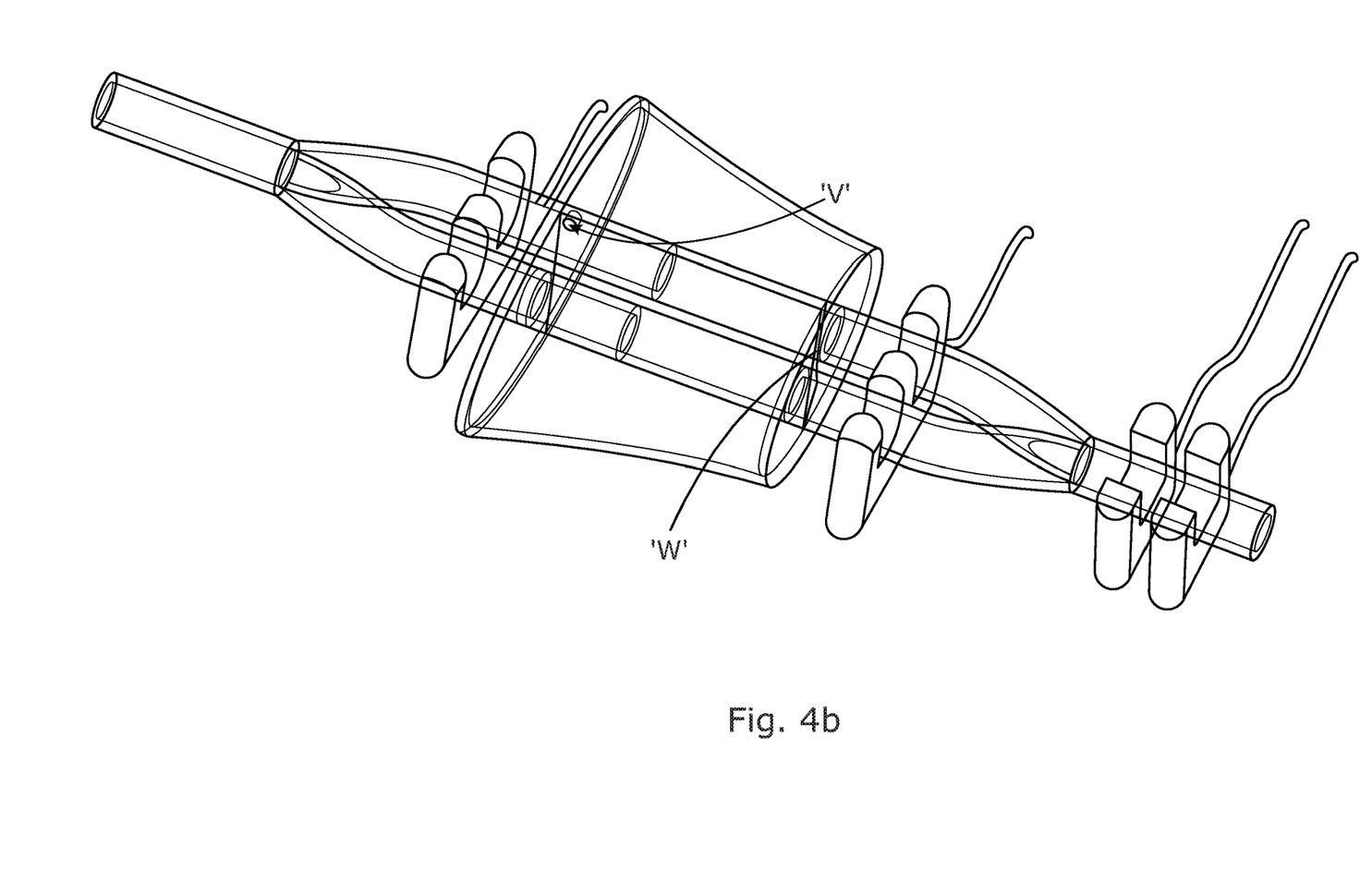

In a first phase, tank 40 is filled. To do this valve 45 is opened, valve 44 is closed and valve 42 opened and valve 43 closed. This is depicted in FIG. 4. This causes tank 40 to fill and tank 41 to empty. To allow this to occur a vent "V" is located in an upper position in the dividing wall "W" between the tanks to allow for air to flow between one tank and the other that would otherwise be trapped as is shown in FIG. 4*b*.

Figure 5:
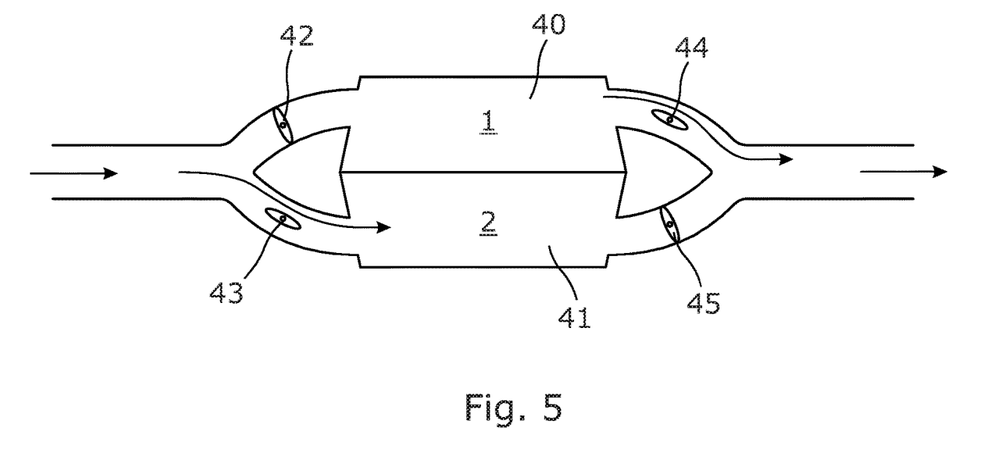

In a second phase, as depicted in FIG. 5, tank 40 is full, and is to be emptied, and tank 41 is empty and is to be filled. The control system 46 signals valve 45 to close and valve 44 to open. At the same time, valve 42 is instructed to close and valve 43 to open.

During this process, the control system monitors the signals of the tank sensors. In the event that the tanks do not empty or empty more slowly than the tank being filled then the control system 46 determines that there is an obstruction downstream of the tanks.

Figure 6:
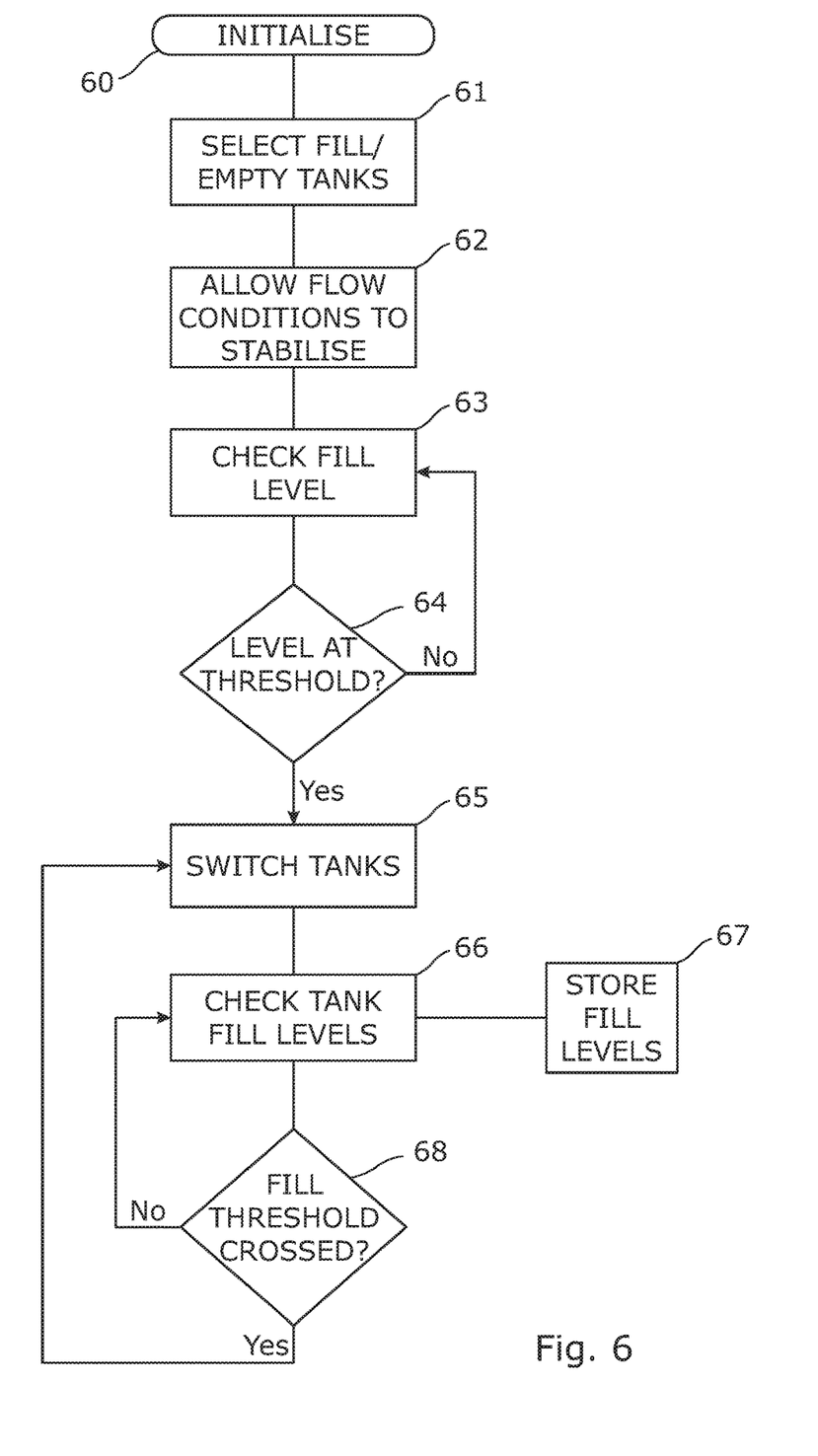
FIGS. 6 and 7 are explanatory diagrams showing the steps performed by the system to determine the presence of a blockage.

The way in which the system operates will now be described with reference to FIGS. 6 and 7.

In a first step 60, the system initialises. This is carried out when the drain is inserted into the patient and the system is switched on by the medical staff. In this step the system "boots up" and performs checks on the various sensors and valves in the system to ensure that they are operational. The status of the system and its components may be indicated on a display to the staff.

In the next step 61, the tank to be filled and the tank to be emptied are selected. In this case tank 40 is selected to be filled first and the tank 41 selected to be emptied. Accordingly, the flow controller 52 is instructed by the processor 50 to set the valves to the correct states. Valve 42 is opened to the forward part of the drain, valve 44 is closed and valve 43 is closed to the forward part of the drain (but opened to atmosphere) and valve 45 opened. Tank 40 then fills as the exudate is drained and tank 41 empties.

In step 62, a period of time is allowed to elapse to allow the exudate flow to be established.

In step 63, the fill level of the tank being filled is determined by the comparator 51 polling the sensors within the tank. The sensor determines the level of the exudate in the tank. This is compared with a predetermined threshold held in memory in step 64 and the comparison repeated. If the threshold is reached, then the tank is considered to be full and the process progresses to step 65.

In step 65 the tanks are switched to the alternative state. That is to say, the tank being filled is selected to be emptied and the tank being emptied is selected to be filled. Following the above, tank 40 is selected to be emptied and tank 41 is selected to be filled. To do this, flow controller 52 is instructed by the processor 50 to switch the valve states. That is to say, valve 42 is closed to the section B (but opened to atmosphere), valve 44 is opened to allow the exudate to flow out of the tank 40. The valve 43 of tank 41 is opened to section B (and closed to atmosphere) and valve 45 is closed. Tank 41 then proceeds to fill.

The tank fill and emptying rates are then determined and stored in memory 53 in steps 66 and 67 by the processor 50 instructing the comparator 51 to provide the outputs of the tank sensors. In this, the exudate levels are checked in the tanks at respective time intervals determined by a system clock (not shown). Thus, the stored states at the particular time intervals provide a rate of filling or emptying of the tanks.

Figure 7:
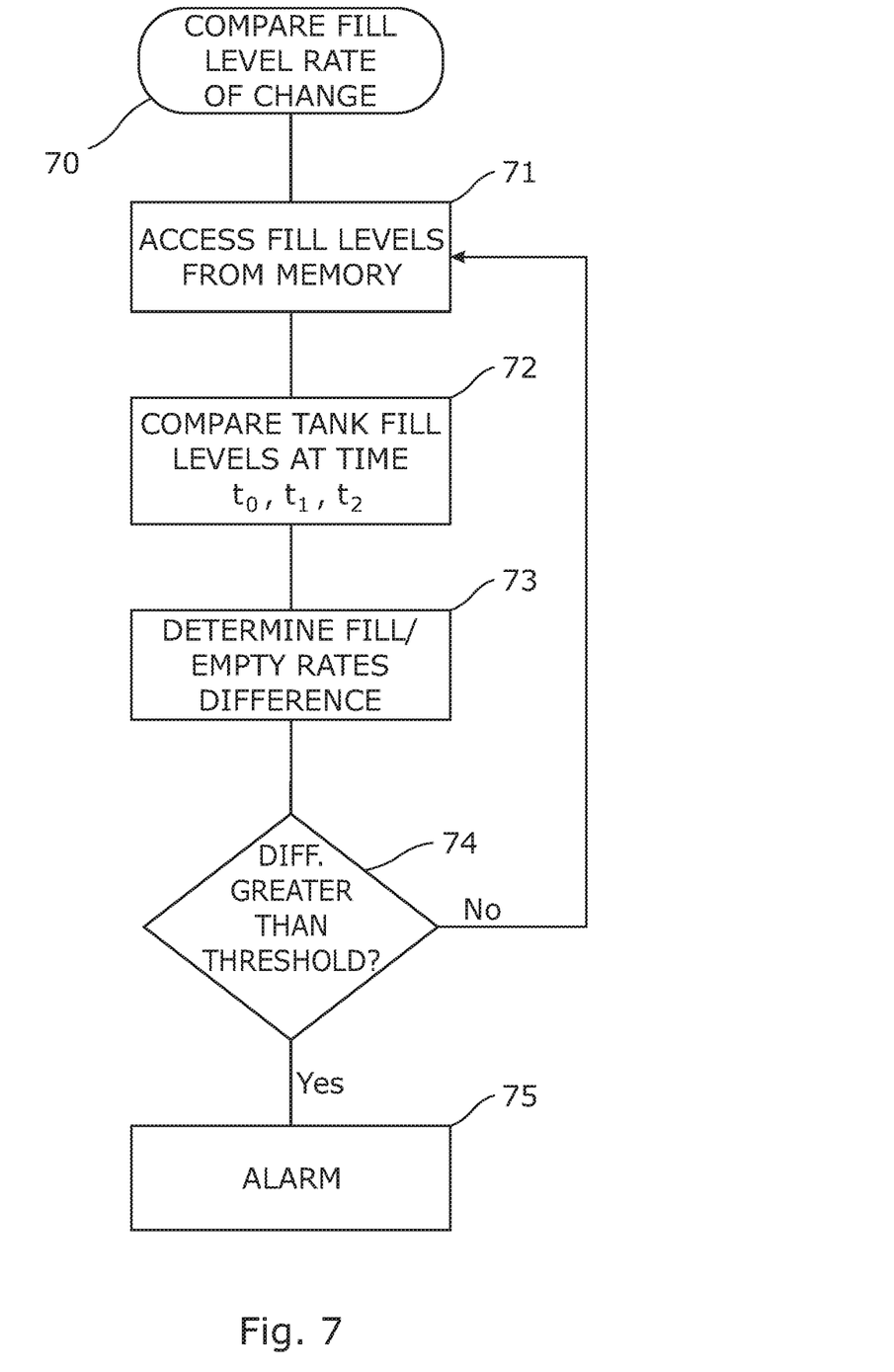

In a process 70 shown in FIG. 7, the processor 50 accesses the stored data from memory 53 in step 71. It then compares the fill levels at the time intervals in step 71, and in step 72, determines the rate of filling and the rate of emptying of the tanks. The average difference in the rate is determined in step 73.

In step 74, the difference in the rate is compared with a predetermined threshold value held in memory 53. If the threshold is not exceeded then the processor accesses the data from memory for the next tank state switching and repeats steps 71 to 74. If the threshold is exceeded, then an alarm is issued in step 75 by suitable instruction from the processor 50 to the alarm device 54.

The medical staff will then be aware of the blockage and may take remedial action by replacing the drain, or parts of it, as required to clear or remove the blockage.

As will be appreciated there will be a number of variations and combinations of features disclosed in the application which will fall within the scope of the recited claims.

What is claimed is:

1. A surgical drain, comprising:
a tube having an inlet portion, an outlet portion, a first branch and a second branch, the tube defining a first flow path including the inlet portion, the first branch and the outlet portion, and the tube defining a second flow path including the inlet portion, the second branch and the outlet portion, wherein the second branch is outside of the first flow path; and
a flow control system configured to monitor flow of fluid filling the first branch and emptying the second branch or emptying the first branch and filling the second branch in an alternate manner.

2. The surgical drain according to claim 1, wherein the flow control system includes a flow controller configured to control flow of fluid through the first branch and the second branch.

3. The surgical drain according to claim 2, wherein the first branch of the tube includes an input valve disposed in communication with the flow controller, and an output valve disposed in communication with the flow controller.

4. The surgical drain according to claim 3, wherein the second branch of the tube includes an input valve disposed in communication with the flow controller, and an output valve disposed in communication with the flow controller.

5. The surgical drain according to claim 1, wherein the flow control system includes a comparator configured to compare rates of fluid flow through the first branch and the second branch.

6. The surgical drain according to claim 5, wherein the flow control system includes an alarm configured to provide an alert in response to an output of the comparator.

7. The surgical drain according to claim 1, further comprising a first sensor disposed within the first branch of the tube and in communication with the flow control system, the first sensor configured to determine a level of fluid within the first branch.

8. The surgical drain according to claim 7, further comprising a second sensor disposed within the second branch of the tube and in communication with the flow control system, the second sensor configured to determine a level of fluid within the second branch.

9. The surgical drain according to claim 1, wherein the first branch includes a first tank, and wherein the second branch includes a second tank.

10. The surgical drain according to claim 9, wherein the first tank and the second tank have nominally identical volumes.

11. The surgical drain according to claim 1, wherein the inlet portion of the tube includes at least one sensor for determining a fluid flow therethrough, and wherein the inlet portion of the tube includes a portion configured for insertion into a patient.

12. The surgical drain according to claim 1, further including a plurality of valves disposed in mechanical cooperation with the tube and configured to direct flow of fluid through one of the first flow path or the second flow path at a particular time.

13. The surgical drain according to claim 1, further including a plurality of valves disposed in mechanical cooperation with the tube and configured to direct flow of fluid through the first flow path and the second flow path in an alternating manner.

14. The surgical drain according to claim 1, wherein fluid configured to flow in the first flow path bypasses the second branch of the tube.

15. The surgical drain according to claim 14, wherein fluid configured to flow in the second flow path bypasses the first branch of the tube.

16. The surgical drain according to claim 1, wherein the tube divides into the first branch and the second branch and then reunites into the outlet portion.

17. A surgical drain, comprising:
a tube having an inlet portion, an outlet portion, a first branch and a second branch, the tube defining a first flow path including the inlet portion, the first branch and the outlet portion, and the tube defining a second flow path including the inlet portion, the second branch and the outlet portion, wherein the first branch and the second branch are arranged in parallel; and
a flow control system including a comparator configured to compare rates of fluid flow through the first branch and the second branch.

18. The surgical drain according to claim 17, further comprising a first sensor disposed within the first branch and in communication with the flow control system, the first sensor configured to determine a level of fluid within the first branch.

19. The surgical drain according to claim 17, further including a plurality of valves disposed in mechanical cooperation with the tube and configured to direct flow of fluid through one of the first flow path or the second flow path at a particular time.

20. The surgical drain according to claim 17, wherein fluid configured to flow in the first flow path bypasses the second branch of the tube, and wherein fluid configured to flow in the second flow path bypasses the first branch of the tube.

* * * * *